Figure 1:
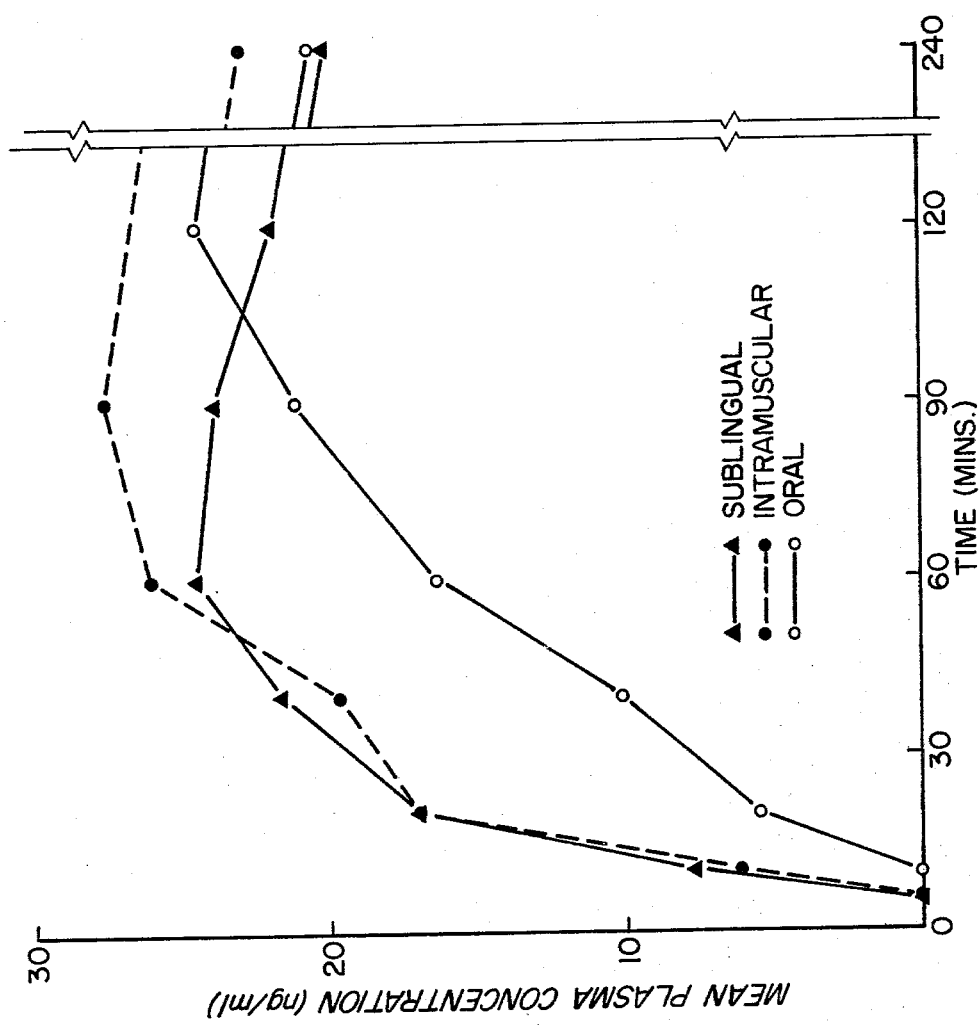

United States Patent [19]

Porter

[11] 4,229,447

[45] Oct. 21, 1980

[54] INTRAORAL METHODS OF USING BENZODIAZEPINES

[75] Inventor: William R. Porter, Etobicoke, Canada

[73] Assignee: American Home Products Corporation, New York, N.Y.

[21] Appl. No.: 44,430

[22] Filed: Jun. 4, 1979

[51] Int. Cl.² ............................................. A61K 31/33

[52] U.S. Cl. .................................................... 424/244

[58] Field of Search ....................................... 424/244

*Primary Examiner*—Stanley J. Friedman
*Attorney, Agent, or Firm*—George Tarnowski

[57] ABSTRACT

A method of therapeutically administering benzodiazepines by the intraoral, i.e. sublingual or buccal route is disclosed.

8 Claims, 1 Drawing Figure

INTRAORAL METHODS OF USING BENZODIAZEPINES

BACKGROUND OF THE INVENTION

The benzodiazepines are well-known central nervous system agents which are therapeutically used in the treatment of anxiety states, neuroses, tension states associated with organic conditions, irritability, as well as the treatment of alcoholics, expecially for the alleviation of the symptons of alcoholic withdrawal or the excited and combative episodes that occur during alcoholic intoxication, and to relieve the anixety and tension associated with alcoholic post-withdrawal.

At the present time, the benzodiazepines are administered by both the oral and the parenteral route. The oral route of administration is the most common in therapeutic practice, but sometimes it is not possible to achieve sufficiently high plasma concentrations to be effective, and some patients occasionally have an absorption malfunction. Moreover, oral administration is precluded for patients with gastrointestinal intolerance, or those in preparation for anesthesia or who have had gastrointestinal surgery.

The parenteral routes of administration, on the other hand, generally lead to very rapid rises in plasma concentration of the therapeutic agent. This is especially true of the intravenous route of administration, in which no delay in the rapid rise of plasma concentration is imposed by absorption. The intramuscular and subcutaneous routes have a fairly rapid during drug absorption profile, and so are likewise desirable routes of administration. However, parenteral administration is often accompanied by pain and irritation at the injection site. Moreover, parenteral routes of administration require sterilization of both the preparatives and the hypodermic syringes. A more significant problem with parenteral routes of administration is that except in a few unique instances, self-administration, which is possible in the case of the oral route, is not practical or even desirable with the parenteral routes.

All the above-mentioned factors hold true with regard to the oral and parenteral routes of administration of the benzodiazepines. Some of the benzodiazepines, as for example oxazepam and lorazepam, at present are not even available in parenteral dosage forms. Therefore, it would be highly desirable to have a dosage form for administration of benzodiazepines which has the ease of administration of the oral route with the rapid attainment of effective plasma concentrations possible with the parenteral routes, and without the disadvantages of either of these two common routes of administration.

It has now been unexpectedly found that the intraoral, i.e. buccal or sublingual, administration of benzodiazepines results in therapeutic effects indistinguishable from those of the parenteral dosage form.

DESCRIPTION OF THE INVENTION

The invention is directed to a method for administering benzodiazepines having the formulae:

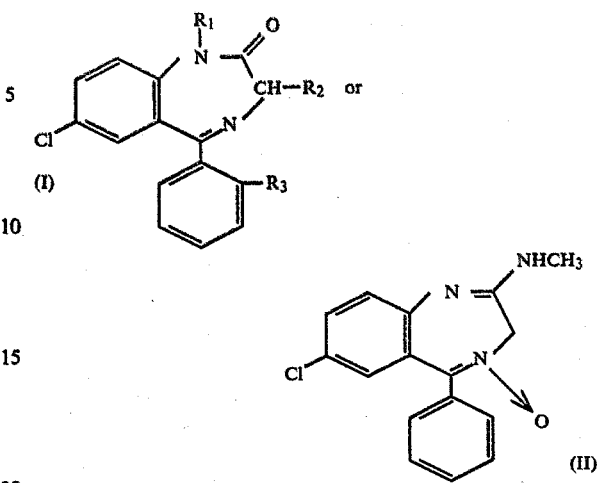

wherein $R_1$ is hydrogen or lower alkyl, $R_2$ is hydrogen or hydroxyl and $R_3$ is hydrogen or chlorine, which comprises sublingually or bucally administering to a human a therapeutically effective amount of the benzodiazepine alone or with an intraorally administrable pharmaceutical carrier.

FIG. 1 is a graphic representation of the results of a bioavailability study of the sublingual, intramuscular and oral administration of lorazepam, expressed as mean plasma concentration versus time of sample collection.

The term "oral administration", when used throughout the specification, refers to the administration of a dosage form by swallowing, so that drug absorption is from the gastrointestinal tract.

The benzodiazepines which may be administered buccally or sublingually include for example 7-chloro-1,3-dihydro-1-methyl-5-phenyl-2H-1,4-benzodiazepin-2-one (diazepam), 7-chloro-5(o-chlorophenyl)-1,3-dihydro-3-hydroxy-2H-1,4-benzodiazepin-2-one (lorazepam), 7-chloro-1,3-dihydro-3-hydroxy-5-phenyl-2H-1,4-benzodiazepin-2-one (oxazepam), 7-chloro-1,3-dihydro-3-hydroxy-1-methyl-5-phenyl-2H-1,4-benzodiazepin-2-one (temazepam) as well as 7-chloro-2-(methylamino)-5-phenyl-3H-1,4-benzodiazepine 4-oxide (chlordiazepoxide).

The benzodiazepines which can be administered by the intraoral, i.e. buccal or sublingual, route are, with the exception of chlordiazepoxide, practically insoluble in water and do not form water soluble physiologically acceptable salts. In view of the water-insoluble character of the benzodiazepines and the lack of acceptable salts, these therapeutic agents are used in their free base form in tablets and in propylene glycol-based injectable dosage forms. It is, therefore, unexpected that these water-insoluble drugs are readily absorbed by the oral mucosa and enter into the bloodstream so rapidly that the intraoral administration can be regarded as a new form of treatment, i.e., parenteral treatment given intraorally.

It is generally recognized that few drugs can be effectively administered sublingually or buccally. The nitrites and organic nitrates are most often administered sublingually for prompt relief of acute angina pectoris attacks, and some steroids and polypeptides, can also be administered intraorally, such as oxytocin and progesterone. However, very few other systemically-acting drugs have been successfully administered intraorally.

The benzodiazepines, however, not only can be successfully administered intraorally, but bioavailability testing shows that the intraoral dosage form is absorbed with much more rapidity than the oral dosage form, thereby giving a significantly more rapid therapeutic effect than is obtainable with the oral dosage form. Pharmacokinetics suggest that the intraoral dosage form is also as rapidly absorbed and the therapeutic effect as rapidly established as is the case with the intramuscular administration of the benzodiazepines.

The buccal dosage form is administered by placing a buccal tablet in the buccal pouch and allowing it to dissolve completely. The sublingual tablet is placed beneath the tongue and allowed to dissolve completely. In all instances, since the absorption of the therapeutic agent is through the oral mucosa, the tablets should not be chewed or swallowed before complete dissolution in the mouth.

The rapid onset of therapeutic effect via the intraoral route of administration can be advantageously used where the oral or parenteral routes of administration are contraindicated or cannot be tolerated. Moreover it is now possible to achieve, by self-administration, the degree and rapidity of therapeutic effect formerly attainable only in the parenteral dosage form.

The intraoral route of administration of benzodiazepines is effectuated with buccal or sublingual tablets prepared with a rapidly disintegrating base. The tablets must conform to the disintegration test limits for buccal and sublingual tablets as set out in the U.S. Pharmacopeia XIX, p. 650.

The sublingual tablets, for example should disintegrate after not more than two minutes, with most tablets disintegrating after 10–12 seconds. Suitable rapidly disintegrating bases will generally consist of a diluent (filler), binder, disintegrating agent, and lubricant. the diluents include lactose, starch, dibasic calcium phosphate and calcium sulfate. The common binders include acacia, gelatin, sucrose, povidone, methylcellulose, carboxymethylcellulose, microcystalline cellulose and hydrolyzed starch pastes. The disintegrating agents include starch, modified starches, alginic acid, microcystalline cellulose, and colloidal silicates, while the commonly used lubricants include the metallic stearates, stearic acid, hydrogenated vegetable oils and talc.

The effective dosage of the benzodiazepines depends upon the severity, the stage, and the individual characteristics of each case and will be determined by an attending physician. Generally, a dosage of from 0.02 to about 10 mg. per kg. of body weight per day constitutes an overall range. Buccal or sublingual tablets of requisite effective dose can be conveniently prepared, by conventional tablet manufacturing procedures.

EXAMPLE 1

7-Chloro-5-(o-Chlorophenyl)-1,3-Dihydro-3-Hydroxy-2H-1,4-benzodiazepin-2-One (Lorazepam) Sublingual Tablets

| Per Tablet: | |
|---|---|
| 1.0 mg. | Lorazepam |
| 10.8 mg. | Microcrystalline Cellulose NF |
| 3.0 mg. | Corn Starch USP |
| 0.1 mg. | Magnesium Stearate USP (up to 5% overage may be used) |
| 21.1 mg. | Lactose USP |
| 36.0 mg. | |

Proportions of inert ingredients may be adjusted to ±10%.

Transfer the lactose, lorazepam, microcrystalline cellulose, corn starch and the magnesium stearate to a suitable mixer and mix well. Pass the powders through a suitable screen. If necessary, densify the powders by slugging or compaction, grind and add additional magnesium stearate, within the formula limitation, as required. Compress the tablets as per conventional methods.

Finished tablet form, when tested according to the USP Procedure for sublingual tablets, have a limit of disintegration of not more than two minutes.

The relative bioavailability of the lorazepam sublingual dosage form of Example 1 was compared with two other formulations of lorazepam. The formulations used are as follows:

A. 1 mg. sublingual tablets (Example 1)—Treatment I
B. 1 mg. intramuscular injection—Treatment II
C. 1 mg. oral tablets—Treatment III Twelve healthy young adult male volunteers were chosen for this experiment, and their mean body weight was 75.43±8.27 kg. Prior to the study, a complete medical assessment was obtained which included a history of a physical examination and routine biochemical tests (blood cells count, blood chemistry and urinalysis). All twelve subjects were found normal.

All volunteers were required not to take any drug 48 hrs. prior to the administration of each formulation to be studied; similarly, alcoholic beverages were prohibited during the 48-hour period preceding the administration of each treatment. No other drug was allowed on test days. None of the subjects had a history of ingestion of known inducers or inhibitors of microsomal enzymes one month prior to the initiation of the study. All subjects were told to keep in a fasting state for the 12-hour period previous to the administration of the formulations. There were no reports of adverse reactions experienced during the two weeks of the study, except sleepiness and drowsiness.

Every subject received each of the three lorazepam dosage forms at a rate of 2 mg. per dose. One week elapsed between test days. The dose was administered to each subject with 200 ml. of water for the tablets and after 200 ml. of water for the sublingual tablets. All subjects fasted for 12 hours prior to and until 4 hours after drug administration. Ten ml. of blood were withdrawn from the antecubital vein before drug ingestion (time 0) and 1/12, 1/6, ⅓, ⅔, 1.5, 2, 4, 6, 8, 12, 24 and 36 hours following drug administration. Blood samples were centrifuged and treated as follows:

Blood was collected in heparinized vacutainers and immediately centrifuged and plasma removed by aspiration, at: 0, 1/12, 1/6, ⅓, ⅔, 1, 1.5, 2, 4, 6, 8, 12, 24 and 36 hours after administration of the different formulations. Plasma specimens were kept under refrigeration until assayed.

The plasma was analyzed in duplicate by gas chromatography and the plasma concentrations for each sample collection determined. The results have been graphically plotted in FIG. 1, in which mean plasma concentration of lorazepam in nanograms per milliliter versus time of sample collection in minutes is plotted for each of the three treatments.

The results, as represented in FIG. 1, show that the sublingual absorption of lorazepam in the first 60 minutes is very significantly greater than from the oral route, the peak level of plasma concentration of lorazepam being achieved 60 minutes after sublingual administration while by the oral route after 120 minutes. These results further clearly demonstrate that the sublingual administration of lorazepam is not only pharmacokinetically indistinguishable from the intramuscular dosage form, but that the sublingual dosage form suggests more rapid absorption and hence more rapid therapeutic effect than the intramuscular dosage form.

What is claimed is:

1. A method for affecting the human central nervous system by the administration of a benzodiazepine having the formula:

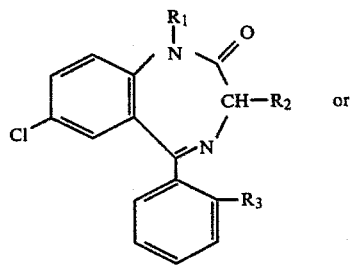 or

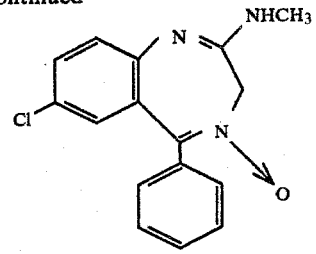

wherein $R_1$ is hydrogen or lower alkyl, $R_2$ is hydrogen or hydroxy, and $R_3$ is hydrogen or chlorine, which comprises sublingually or buccally administering to a human a therapeutically effective amount of said benzodiazepine.

2. The method of claim 1, wherein said benzodiazepine is administered with an intraorally administrable pharmaceutical carrier.

3. The method of claim 1, wherein $R_1$ is hydrogen, $R_2$ is hydroxy, and $R_3$ is hydrogen.

4. The method of claim 1, wherein $R_1$ is hydrogen, $R_2$ is hydroxy, and $R_3$ is chlorine.

5. The method of claim 1, wherein $R_1$ is methyl, $R_2$ is hydroxy, and $R_3$ is hydrogen.

6. The method of claim 1, wherein $R_1$ is methyl, $R_2$ is hydroxy, and $R_3$ is chlorine.

7. The method of claim 1, wherein $R_1$ is methyl, $R_2$ is hydrogen and $R_3$ is hydrogen.

8. The method of claim 1, wherein said benzodiazepine is 7-chloro-2-(methylamino)-5-phenyl-3H-1,4-benzodiazepine 4-oxide and physiologically acceptable salts thereof.

* * * * *